US008342684B2

(12) United States Patent
Ho et al.

(10) Patent No.: US 8,342,684 B2
(45) Date of Patent: Jan. 1, 2013

(54) DETERMINATION OF OPTICAL ADJUSTMENTS FOR RETARDING MYOPIA PROGRESSION

(75) Inventors: Arthur Ho, Coogee (AU); Klaus Ehrmann, Manly (AU)

(73) Assignee: The Institute for Eye Research Limited, Sydney, New South Wales (AU)

( * ) Notice: Subject to any disclaimer, the term of this patent is extended or adjusted under 35 U.S.C. 154(b) by 208 days.

(21) Appl. No.: 12/597,890

(22) PCT Filed: Apr. 28, 2008

(86) PCT No.: PCT/AU2008/000572
§ 371 (c)(1),
(2), (4) Date: Aug. 3, 2010

(87) PCT Pub. No.: WO2008/131479
PCT Pub. Date: Nov. 6, 2008

(65) Prior Publication Data
US 2010/0296058 A1 Nov. 25, 2010

(30) Foreign Application Priority Data

Apr. 27, 2007 (AU) ................................ 2007902208

(51) Int. Cl.
*G02C 7/02* (2006.01)
*G02B 7/00* (2006.01)
(52) U.S. Cl. ............................... 351/159.79; 351/159.74
(58) Field of Classification Search . 351/159.73–159.81
See application file for complete search history.

(56) References Cited

U.S. PATENT DOCUMENTS 5,252,998 A * 10/1993 Reis et al. ................. 351/160 R
5,541,678 A * 7/1996 Awanohara et al. .......... 351/161
5,777,719 A 7/1998 Williams et al.
(Continued)

FOREIGN PATENT DOCUMENTS
WO WO 2008/098293 A1 8/2008
(Continued)

OTHER PUBLICATIONS

Pacella, Rosanna, James McLellan, Kenneth Grice, Elizabeth A. Del Bono, Janey L. Wiggs, and Jane E. Gwiazda. "Role of Genetic Factors in the Etiology of Juvenile-Onset Myopia Based on a Longitudinal Study of Refractive Error." Optometry and Vision Science 76.6 (1999): 381-386. Print.*

(Continued)

*Primary Examiner* — Ricky Mack
*Assistant Examiner* — Zachary Wilkes
(74) *Attorney, Agent, or Firm* — Merchant & Gould P.C.

(57) ABSTRACT

A method or process for providing an anti-myopia lens or treatment for a patient's eye with progressive myopia, which involves (in one form) generating biometric data relating to the central and peripheral refractive errors of the eye, optionally together with data relating to the patient's visual or lifestyle needs and the patient's predisposition to progressive myopia. This data is input to a processor or algorithm that generates a basic lens design, a customised design or a program for reshaping the cornea of the eye. The selected modality is applied to the patient and its suitability is assessed with the result of the assessment feedback to the algorithm to generate a refined output design, which is applied to the patient. The process is repeated at intervals to check continued myopia progression and adjust the design of the selected modality after further measurement.

20 Claims, 5 Drawing Sheets

U.S. PATENT DOCUMENTS

| | | | |
|---|---|---|---|
| 5,796,463 | A | 8/1998 | Bullimore |
| 6,045,578 | A | 4/2000 | Collins et al. |
| 6,343,861 | B1 | 2/2002 | Kris et al. |
| 6,663,240 | B2 | 12/2003 | Patel |
| 6,752,499 | B2 | 6/2004 | Aller |
| 7,025,460 | B2 | 4/2006 | Smitth et al. |
| 2003/0107706 | A1 | 6/2003 | Rubinstein et al. |
| 2004/0246440 | A1 | 12/2004 | Andino et al. |
| 2006/0082729 | A1 | 4/2006 | To et al. |
| 2006/0116759 | A1 | 6/2006 | Thornton et al. |
| 2006/0232743 | A1 | 10/2006 | Legerton |
| 2006/0264917 | A1 | 11/2006 | Tuan et al. |
| 2007/0159601 | A1 | 7/2007 | Ho et al. |
| 2008/0062380 | A1 | 3/2008 | Phillips |

FOREIGN PATENT DOCUMENTS

| | | | |
|---|---|---|---|
| WO | WO 2008/116270 A1 | 10/2008 | |

OTHER PUBLICATIONS

Atchison et al. "Shape of the Retinal Surface in Emmetropia and Myopia." *Investigative Ophthalmology & Visual Science*, Aug. 2005, vol. 46, No. 8, pp. 2698-2707.

Mutti et al. "Peripheral Refraction and Ocular Shape in Children." *Investigative Ophthalmology & Visual Science*, Apr. 2000, vol. 41, No. 5, pp. 1022-1030.

Saw et al. "Interventions to retard myopia progression in children: an evidence-based update." *Ophthalmolog*,. vol. 109, Issue 3, pp. 415-421 (Mar. 2002). Abstract Only.

Schmid, Gregor F. "Variability of retinal steepness at the posterior pole in children 7-15 years of age." *Current Eye Research*. vol. 27, No. 1, 2003, pp. 61-68. Abstract Only.

Extended European Search Report for corresponding European Patent Application No. 08733399.3 mailed Dec. 29, 2011.

\* cited by examiner

DETERMINATION OF OPTICAL ADJUSTMENTS FOR RETARDING MYOPIA PROGRESSION

This application is a National Stage Application of PCT/AU2008/000572, filed Apr. 28, 2008, which claims benefit of Serial No. 2007902208, filed Apr. 27, 2007 in Australia and which applications are incorporated herein by reference. To the extent appropriate, a claim of priority is made to each of the above disclosed applications.

BACKGROUND OF THE INVENTION

1. Technical Field

This invention relates to means for determining, specifying or prescribing adjustment or modification of the optics of the human eye by use of ophthalmic lenses or cornea shaping for the purpose of retarding, mitigating or controlling the progression of myopia. It also relates to ophthalmic correction devices, methods and associated therapies.

The adjustments or modifications concerned can be effected by the fitting of spectacle or contact lenses or, less preferably, by modification of corneal shape through orthokeratology, corneal onlays or inlays, laser ablation and other forms of surgical intervention.

2. Discussion of Related Art

U.S. Pat. No. 7,025,460 to Smith et al and associated publications in the scientific literature show that the excessive eye growth associated with myopia—particularly in the young—is related to the focus of the peripheral retinal image and, more specifically, that myopia is encouraged where the focal plane of peripheral vision lies posterior of the retina and is discouraged or inhibited where it lies anterior to the retina. Lens designs based on this theory that provide both clear central vision and sufficient curvature of the peripheral focal plane were disclosed by Smith et al and are herein referred to as 'anti-myopia' lenses. Others have since disclosed various modifications and improvements of anti-myopia lenses for specific situations (see for example, Ho et al, US 20070159601).

Until the disclosures of Smith et al, it had been thought that myopia development had to do with some feature of central or paraxial vision and various methods of effecting selective defocus of the central image were proposed to inhibit myopia progression. As a result, central vision was impaired in one way or another in the attempt to inhibit myopia progression. For relevant prior patent disclosures see for example, Collins et al U.S. Pat. No. 6,045,578, Kris et al U.S. Pat. No. 6,343,861, Aller U.S. Pat. No. 6,752,499, Phillips US 2008062380, and, To US 2006/0082729. For relevant scientific publications see for example, Atchison, et al. "Shape of the Retinal Surface in Emmetropia and Myopia" (Invest Opthalmol Vis Sci. 2005: 46: 2698-2707); Mutti, et al. "Peripheral Refraction and Ocular Shape in Children" (Invest Opthalmol Vis Sci. 2000; 41:1022-1030); Saw, et al. "Interventions to Retard Myopia Progression in Children, An Evidence-based Update Opthalmology" (2002, Vol. 109, 3, 415-421); Schmid, "Variability of retinal steepness at the posterior pole in children 7-15 years of age" (Current Eye Research 2003, Vol. to 27, No. 1, pp. 61-68).

Traditionally, central vision correction for the myope (as opposed to the inhibition of progressive myopia) has been concerned with lower order aberrations that are readily measured using instruments commonly available to optometrists and are the major factors determining central visual acuity. The lower order aberrations concerned are essentially refractive error and astigmatism, which includes spherical and cylindrical components quantified in terms dioptric power and the orientation of cylindrical axis. These are specified or reflected in a typical ophthalmic prescription. Appropriate lenses can be obtained from such prescriptions using widely available computer-based design methods, or obtained from pre-manufactured lens stock. More detailed data, such as present cornea shape, will need to be provided were modification of cornea shape is desired.

More recently, techniques have been developed to further improve central visual acuity by correcting for higher order aberrations using wavefront techniques to prescribe and generate custom made contact lenses, spectacles, wave plates or corneal reshaping (see for example, Tuan US 2006/0264917, Andino US 2004/0246440, Rubinstein US 2003/0107706, Patel, U.S. Pat. No. 6,663,240 and Williams U.S. Pat. No. 5,777,719).

While the traditional methods that correct lower order aberrations provide good central vision for most myopes, they have the unfortunate side-effect of shifting the peripheral focal plane further behind the retina, rendering the patient more hyperopic in the periphery and giving added stimulus for eye elongation. And, while modern techniques that address both lower and higher order aberrations can provide excellent central vision, they can also have the same undesirable side effect in the periphery. On the other hand, the application of the teachings of Smith et al is not straight forward as it fails to adjust for important patient-related factors, allow for the problems of disturbing peripheral blur or recognise the role of conventional refractive correction in creating peripheral hyperopia.

BRIEF SUMMARY OF THE INVENTION

The present invention involves the provision of anti-myopia lenses, lens designs and treatments based thereon, which are customised to the needs of the patient and which allow for extended treatment periods involving repeated refinement of lenses and treatments to control the progression of myopia and match changing need. A variety of factors are identified as being of importance in customising anti-myopia lenses and treatments. These principally include predisposition to myopia, lifestyle and the biometric characteristics of the eye, though many other secondary factors may be taken into account. Preferably, this is done by the use of a suitable computer processor algorithm that adjusts peripheral myopic defocus, though manual or semi-manual methods for implementing customisation are herein envisaged. A procedure for checking the acceptability of the resultant myopic defocus to the patient is also a preferred element of customisation.

As with normal anti-myopia lenses, the methods of the invention aim to provide clear central vision free of significant lower order and, preferably, higher order aberrations. The area of clear central vision preferably corresponds with normal pupil diameter; that is, an area that subtends an angle of about 10° from the optic axis. The peripheral area of therapeutic myopic defocus will normally be annular and lie above 20° from the optical axis. However, the size of the central zone and the location of the peripheral zone are factors that can be adjusted as part of the customisation process. For example, an adult patient who is determined to have a low predisposition to progressive myopia, who spends much of the day outside or who is actively involved in field sports can, by the customisation process, have the central zone of clear vision expanded to at least 20° and the peripheral myopic defocus zone pushed out to above 30°. Alternatively, a child of 10 who is hyperopic in the periphery, has myopic immediate family members and spends most of the day inside may need a larger peripheral zone of myopic defocus with greater refractive power, to the point where tolerability and compliance could be limiting factors. In that case, frequent follow-up would be desirable. As a guide, we have found that the risk of young myopes having or developing progressive myopia increases the younger the patient is than the average age of puberty in the society or the expected age of puberty for the patient. A useful fixed age for reference is 12; that is, the risk of progressive myopia increases with the number of years that the patient is under 12.

Another factor to be used in customising a lens or treatment for a patient is genetic predisposition to progressive myopia. While we know of no human gene that has been reliably associated with progressive myopia, familial association is well known and incorporates a complex combination of environmental, behavioural and genetic factors. Accordingly, we have found that a suitable proxy for genetic predisposition to progressive myopia is the degree to which the patient's parents and immediate family suffer from myopia; a simple index being the average myopia (in terms of dioptric power) of the four eyes of the parents.

Other factors predisposing a person to progressive myopia are lifestyle (alluded to above) and the level of peripheral hyperopia (as first pointed out by Smith et al). Lifestyle factors mainly relate to close-work vs. outdoor-time, but there are many aspects of this. While lens or treatment customisation needs to reflect propensity to progressive myopia, it also needs to be sensitive to the lifestyle needs of the patient. Patients that do more close-work can tolerate more intrusive peripheral myopic defocus than patients who are involved with outdoor sports or jobs. As pointed out above, the level of peripheral myopia in a patient that does not use conventional corrective lenses is a good indicator of disposition to progressive myopia, but many patients examined by a practitioner for the first time will have been wearing corrective lenses for some time. These lenses can greatly increase peripheral hyperopia when fitted and cause the natural eye to compensate by shifting the peripheral focus forwards so that, when the eye is examined alone, it already has peripheral myopic defocus, which indicates that lens customisation need not correct peripheral aberration. It should be borne in mind that the use of counter-productive conventional lenses complicates the matter of familial or genetic predisposition since progressive myopia might have been 'artificially' induced in the parents eyes.

Of course, design of the basic anti-myopia lens or cornea shape requires the input of biometric data relevant to the eye in question. Ideally, this would include a map of the aberrations of the eye over the surface of the eye from the axis to around 50° and such eye maps are now readily obtainable by use of an instrument disclosed in copending international patent application PCT/AU2008/000183 and are applicable to the correction of both lower and higher order aberrations in both areas. Of particular interest are peripheral aberration readings near the horizontal meridian of the eye, especially in the temporal quadrant as we believe that the stimulus for eye growth is especially strong when there is hyperopic defocus in is this area. In addition, other biometric data such as pupil size, pupil decentration, axial eye-length, angle kappa and cornea shape can be used. However, a single central refraction reading and one or a few near-peripheral (20°-30°) readings undertaken by conventional means are a tolerable minimum.

For both simplicity and efficacy of myopia control, it is preferred that the regions of the retina where aberration is measured include the peripheral nasal and temporal region on or near the horizontal meridian. The peripheral angles interrogated can range from somewhat less than 20° to somewhat more than 50° with respect to the optical axis of the eye. Interrogations of the vertical or oblique meridians can be added to obtain peripheral refraction data and to identify asymmetries.

The algorithm, method or process for deriving the custom lens or cornea shape is based on—or preferably an addition to—a known lens design program capable of generating a basic lens or cornea shape from input aberration data to correct both central and peripheral aberrations. The adjustment algorithm or method is then used to modify or customise this base design using the patient specific data indicated above to generate an initial or basic customised design. A further level of customisation can then be gained by fitting the basic customised lens, testing it, inputting further information to the algorithm and generating a further stage of customisation. The process is desirably repeated a regular intervals to generate repeated customisations to match the changing characteristics of the eye. Much the same customisation process can be followed with cornea shaping. Depending upon the availability of reliable peripheral aberration measurements, the customisation process may include the production of rotationally asymmetric shapes. Preferably, the customised shapes should ensure that both the sagittal and tangential focal planes fall onto or in front of the retina, but these conditions may be visually unacceptable to individual patients and trial fittings are desirable.

From another aspect of the invention, longitudinal data of peripheral refraction can be obtained from eyes under treatment and treatment efficacy evaluated in terms of the reduction in the progression of myopia. Subjects, who respond well to the optical intervention, can be prescribed with vision correction devices that induce is less peripheral myopic defocus, thus improving all-round vision. On the other hand, if myopia progression is not slowed adequately, the intervention can be modified to provide more peripheral myopic defocus and/or to change the modified peripheral area to achieve better efficacy.

From another aspect, it is preferable that determination of the focal plane of the eye include the central or paraxial region as well as the peripheral regions indicated above so that the correction needed to provide high acuity for central vision can be determined. It is then preferable (as would be normal prescribing practice) to fit test lenses to obtain optimum acuity for central vision using charts or the like and relying upon patient feedback. Where the optimum acuity derived in this way indicates a corrective refractive power for central vision that differs from the basic (initially determined) corrective power by a noticeable amount (usually ¼ D or more), then it is preferable to adjust or correct the determined peripheral power by the same amount and to adjust the prescription in the peripheral region accordingly. Thus, for example, if it is determined (by the measurements indicated above) that the focal plane in the central region of an eye lies anterior to the retina by an amount equivalent to +3 D but patient feedback from the use of test lenses and charts suggests that optimal correction is −2½ D, then the entire determined focal plane needs to be shifted anteriorly by −½ D. The prescription for the peripheral region may then need to be adjusted to ensure that the peripheral focal plane at is brought forward onto or anterior of the peripheral retina.

One aspect of the invention provides a method of determining a customised refractive correction for an eye of a patient to inhibit the progression of myopia in that eye, the eye having a central optic axis, a temporal quadrant, a nasal quadrant and a horizontal meridian passing through the temporal and nasal quadrants, said method comprising the steps of: measuring central aberrations within a central area of the eye that subtends an angle of less than 10° from the optic axis sufficient to specify a base central correction of said central aberrations that will provide clear vision in a central zone of the eye, measuring peripheral aberrations in an annular peripheral area of the eye that subtends angles greater than 20° from the optical axis sufficient to specify a base peripheral correction of said peripheral aberrations in a peripheral zone of the eye, and modifying said base peripheral correction to incorporate an amount of myopic defocus determined by at least one of (a) the patient's predisposition to myopia, (b) the patient's lifestyle, and (c) the nature and degree of said peripheral aberrations of the eye, to thereby create a base customised refractive correction for that eye.

The method may further include the steps of determining said patient's predisposition to myopia by having regard to at least one of (a) the patient's genetic predisposition and (b) the patient's youthfulness.

The method may further include the steps of having regard to said genetic predisposition by averaging the central refractive errors of the four eyes of the patient's parents to obtain an average myopic error, and increasing said myopic defocus according to the magnitude of said average myopic error.

The method may further include the steps of having regard to said patient's youthfulness by determining how much younger the patient is than the patient's expected age of puberty, and increasing said myopic defocus and/or the extent of said peripheral zone according said youthfulness.

The method may further include the steps of determining said patient's lifestyle by having regard to the ratio of time spent by the patient indoors and outdoors, and modifying the magnitude of said myopic defocus and/or the extent of said peripheral zone according the magnitude of said ratio.

The method may further include the steps of determining said patient's lifestyle by having regard to the importance assigned by the patient to the playing of outdoor sport, and reducing said myopic defocus and/or the extent of said peripheral zone in accordance with said assigned importance.

The method may further include the steps of determining said nature and degree of said peripheral aberrations by having regard to the degree of hyperopia or myopia in said peripheral area of the eye, increasing said myopic defocus according to the magnitude of said hyperopia, and decreasing said myopic defocus according to the magnitude of said myopia.

The method may further include the steps of applying said base customised refractive correction to the eye of the patient by shaping the cornea of the eye, determining the performance of the eye with the shaped cornea by assessing at least one of (a) patient acceptance of peripheral blur, (b) acuity of central vision and (c) location of peripheral focus, and modifying said customised base refractive correction to improve said determined performance in a further level of customisation.

The method may further include the steps of applying said base customised refractive correction to the eye of the patient by the fitting of an ophthalmic lens, determining the combined performance of the eye and said lens by assessing at least one of (a) patient acceptance of peripheral blur, (b) acuity of central vision and (c) location of peripheral focus, and modifying said customised base refractive correction to improve said determined performance in a further level of customisation.

The customised base refractive correction may be modified by changing the degree of peripheral myopic defocus, varying the size of said peripheral area and/or by enlarging the size of the central area.

The step of measuring peripheral aberrations may include making multiple measurements of peripheral aberration on or near the horizontal meridian of the of the eye and averaging said measurements to specify a base peripheral correction that is rotationally symmetric with respect to the optical axis of the eye.

The step of determining peripheral aberrations may comprise making multiple measurements of peripheral aberration in multiple quadrants of the eye at multiple peripheral angles between 20° and 50° with respect to the optical axis of the eye, and said base peripheral correction is rotationally asymmetric with respect to the optical axis of the eye.

In a further aspect the present invention provides a method for providing a customised anti-myopia lens for inhibiting the progression of myopia in the eye of a patient, the eye having an optical axis, a temporal quadrant, a nasal quadrant and a horizontal meridian passing through the temporal and nasal quadrants, the method comprising the steps of: generating a base lens design, having: a central zone with a refractive power or powers for correcting central aberrations of the eye based upon central measurements of aberration of the eye made at angles of less than 10° with respect to the optic axis, and having an annular peripheral zone surrounding said central zone with a refractive peripheral power or powers for correcting peripheral aberrations of the eye based upon peripheral measurements of aberration of the eye made at angles of at least 20° with respect to the optical axis, and employing said base lens design to obtain a base lens, fitting said base lens to the eye of the patient, obtaining combined central aberration measurements of the combination of the base lens and the eye, obtaining combined peripheral aberration measurements of the combination of the base lens and the eye, modifying said peripheral power or powers of the base lens design using an algorithm having input parameters including at least one of (a) the patient's predisposition to myopia, (b) the patient's lifestyle, (c) acceptability of peripheral blur to the patient, (d) said combined central aberration measurements, and (e) said combined peripheral aberration measurements, to thereby create a customised lens design for the eye, and employing said customised lens design to obtain a customised lens for the eye.

The method may further include the steps of determining said patient's predisposition to myopia by having regard to at least one of (a) the patient's genetic predisposition, (b) the patient's youthfulness, and (c) the degree of hyperopic defocus in the periphery of the eye, modifying the peripheral power or powers of the base lens design by increasing peripheral myopic defocus, and/or by modifying the size of the peripheral zone of the base lens design, according to the determined predisposition.

The method may further include the steps of having regard to said genetic predisposition by averaging the central refractive errors of the patient's immediate blood relatives to obtain an average myopic error, and modifying the peripheral power or powers of the base lens design by increasing peripheral myopic defocus and/or the size of the peripheral zone according to the magnitude of said average myopic error.

The method may further include the steps of having regard to said patient's youthfulness by determining how much younger the patient is than the patient's expected age of puberty, and modifying the peripheral power or powers of the base lens design by increasing peripheral myopic defocus and/or the extent of said peripheral zone according said youthfulness.

The method may further include the steps of determining said patient's lifestyle by having regard to the ratio of time spent by the patient indoors and outdoors, and modifying the peripheral power or powers of the base lens design by increasing peripheral myopic defocus, and/or by modifying the size of the peripheral zone of the base lens design, according to the determined ratio.

The method may further include the steps of determining said patient's lifestyle by having regard to the importance assigned by the patient to the playing of outdoor sport or vehicle driving, and modifying the peripheral power or powers of the base lens design by reducing peripheral myopic defocus and/or the size of said peripheral zone in accordance with said assigned importance.

The method may further include the steps of using said combined central aberration measurements to change the central power of the base lens in both the central zone and the peripheral by the same amount so as to minimise the measured combined central aberration, and modifying said peripheral power or powers of the base lens to reverse said change of power in peripheral zone by the same amount.

The method may further include the steps of using said combined peripheral aberration measurements to modify the power of the power or powers of the peripheral zone of the base lens to ensure a degree of peripheral myopic defocus.

The peripheral measurements of aberration of the eye may include multiple peripheral measurements of peripheral aberration on or near the horizontal meridian of the of the eye, and the method may further include the step of: averaging said multiple peripheral measurements so as to generate a base lens design that is rotationally symmetric.

The peripheral measurements of aberration of the eye may include multiple peripheral measurements of peripheral aberration taken in multiple quadrants of the eye, said multiple quadrants including at least the temporal and nasal quadrants, at multiple peripheral angles between 20° and 50° with respect to the optical axis of the eye, so as to generate a base lens design that is rotationally asymmetric.

In a further aspect the present invention provides a method for treating a patient for progressive myopia in an eye, the method comprising fitting a customised anti-myopia lens to that eye, said lens having been generated by a method as described in the above statements.

In a further aspect the present invention provides a method for providing customised vision correction to an eye of a patient to inhibit the onset or progression of myopia in the eye, the eye having an optic axis, a cornea and a retina, an eye-length comprising the distance between the cornea and retina, a nasal quadrant and a temporal quadrant, the method including the steps of: engaging the patient in a primary clinical consultation and determining primary patient data comprising: date of birth or age, severity of familial myopia, a measurement of the central refractive error of the eye, and at least one measurement of peripheral refractive error for the eye at angles relative to the optic axis of at least 20° in at least the temporal quadrant in terms of spherical equivalent, tangential component of astigmatism and/or sagittal component of astigmatism, and inputting said primary patient data into processor means having an algorithm adapted to generate a design or prescription for a primary customised lens having a central zone adapted to provide clear central vision for the eye and having a surrounding annular peripheral zone lying outside 20° relative to the optic axis and having a degree of myopic defocus determined by said algorithm, and fitting the patient with said primary customised lens.

The primary patient data may include a primary measurement of eye-length, said primary measurement of eye-length being input with said primary patient data into said processor means.

The method may further include the steps of determining the patient's lifestyle in terms of outdoor vs. indoor activities, participation in team sport and/or the amount of vehicle driving, parameterising the determined lifestyle, and including said parameterised lifestyle with said primary patient data input into said processor means.

The patient's lifestyle may be determined by interview.

The method may further include the steps of validating the primary customised lens as fitted to the patient by generating primary validation data including: measurement of the acuity of the central vision of the eye and lens combination, measurement of peripheral myopic defocus of the eye and lens combination, an assessment of the acceptability of peripheral blur perceived by the patient, inputting said primary validation data to said processor and algorithm to generate a validated design or prescription for a validated primary customised lens, and providing said validated customised lens to the patient.

The method may further include the steps of engaging the patient in a secondary clinical consultation subsequent to said primary clinical consultation and determining secondary patient data comprising: a further measurement of the central refractive error of the eye without said primary customised lens in place, a measurement of the combined central refractive error of the eye with said primary customised lens fitted to the eye, a further measurement of peripheral refractive error of the eye without said primary customised lens in place, a measurement of the combined peripheral refractive error of the eye and the lens with said primary customised lens in place, a further measurement of eye-length, inputting said secondary patient data into said processor means and said algorithm to generate a secondary design or prescription for a secondary customised lens having a central zone adapted to provide clear central vision for the eye and having a surrounding annular peripheral zone lying outside 20° relative to the optic axis and having a degree of myopic defocus determined by said algorithm, and fitting the patient with said secondary customised lens.

In a further aspect the present invention provides a method for providing a customised anti-myopia lens for the eye of a patient, the eye having an optical axis, the method comprising the steps of: generating a base lens design, having: a central zone with a refractive central power for correcting central aberrations of the eye based upon central measurements of aberration of the eye made at angles of less than 10° with respect to the optic axis, and having an annular peripheral zone surrounding said central zone with a refractive peripheral power or powers for correcting peripheral aberrations of the eye based upon peripheral measurements of aberration of the eye made at angles of at least 20° with respect to the optical axis, and employing said base lens design to obtain a base lens, fitting said base lens to the eye of the patient, obtaining combined central aberration measurements of the combination of the base lens and the eye to determine an adjustment of said central power to optimise central vision, making said power adjustment to both the central and peripheral zone of the lens, and removing said power adjustment from the peripheral zone, to create a customised lens design and providing said customised lens for the eye.

DETAILED DESCRIPTION OF EXAMPLES OF THE INVENTION

Having broadly portrayed the invention in the above summary, examples of the implementation of the invention will now be described with reference to the accompanying drawings for the purpose of illustration.

BRIEF SUMMARY OF THE VARIOUS VIEWS OF THE DRAWINGS

An example of a suitable instrument for determining the location and configuration of the focal plane (ie, the refractive error) of a natural human eye is described in copending international patent application PCT/2008/000434 and the disclosure of that application is incorporated herein. However, for convenience, the instrument will be now be briefly described with reference to FIG. 1 in which the instrument is generally indicated at 10, this Figure being derived from the aforesaid copending application.

Figure 1:
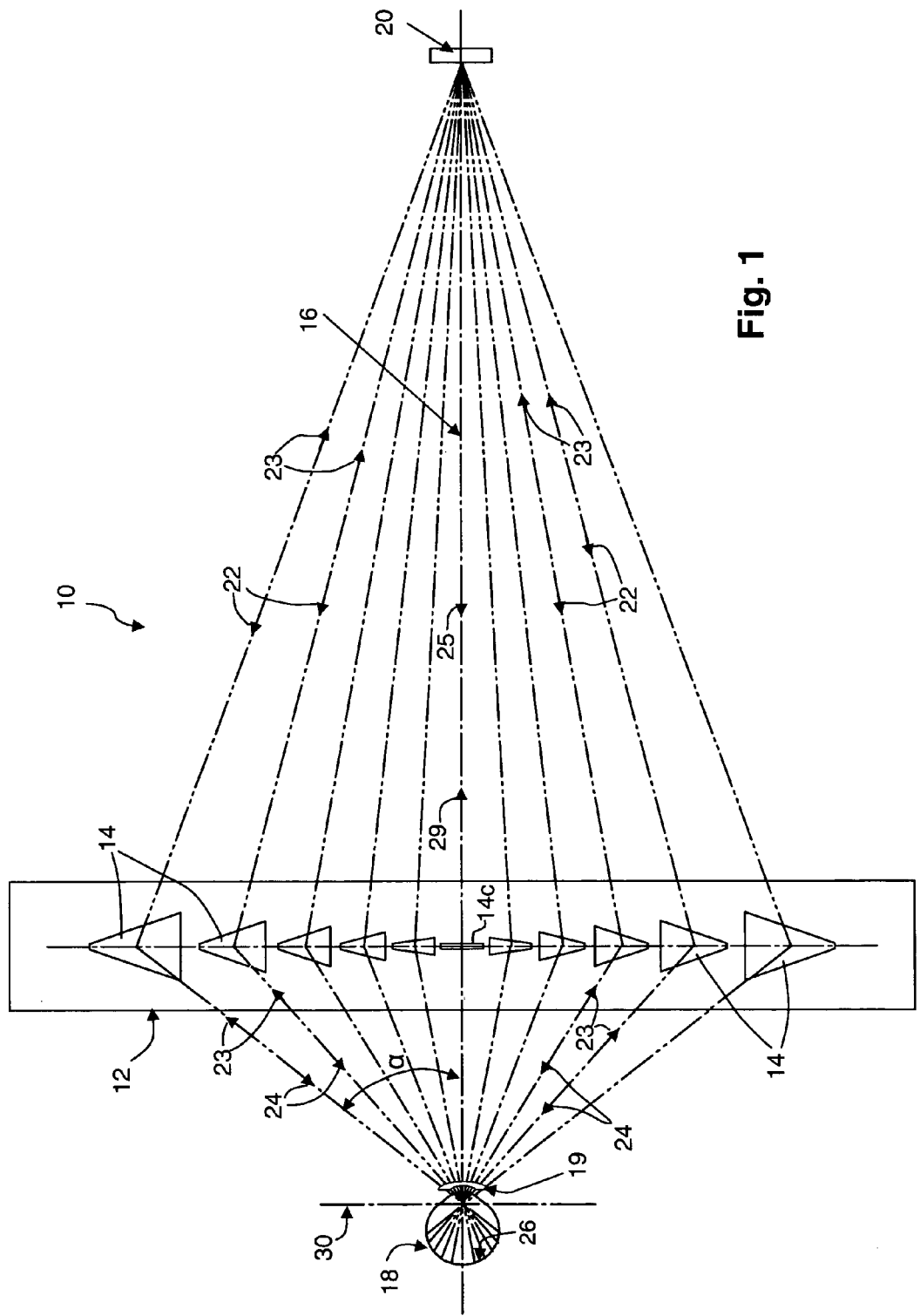
FIG. 1 is a diagrammatic plan view of an instrument suitable for use in determining the peripheral focal plane of a human eye.

Instrument 10 includes a horizontal linear array 12 of deflector elements 14 that extends across the optical axis 16 of the eye 18 under investigation. Eye 18 optionally may be fitted with an ophthalmic correction device such as a lens 19. In FIG. 1, an undifferentiated unit 20 arranged on axis 16 includes an illuminating light source, a controlling computer or processor and a return-beam detector. Unit 20 directs illuminating beams, indicated by arrows 22, sequentially to array elements 14 to generate a corresponding sequence of interrogating beams, indicated by arrows 24, that are directed into eye 18 at different peripheral angles relative to axis 16. Return beams, indicated by arrows 23, are returned from interfaces in the eye, such as the retina 26 or the cornea (not identified in FIG. 1) along the paths of beams 24 and 22 to unit 20 for detection and analysis. A is central illuminating beam 25, a corresponding central interrogation beam (not identified in FIG. 1) and a corresponding central return beam 29 travel along optical axis 16 in a similar manner.

In this instrument, beam deflector elements 14 are prisms (except for central element 14c) that have apex angles such that the respective interrogation beams 24 are directed into eye 18 and the respective return beams 23 are directed to unit 20. Central element 14c does not deflect the illuminating beam and may be a parallel-sided plain glass, as shown, or omitted entirely. Non-horizontal meridians of the eye can be investigated by simply rotating the instrument 10 about optic axis 16 relative to eye 18. Thus, successive interrogation/return beam pairs diverge/converge at successively larger/smaller peripheral angles with respect to axis 16 as they pass into and out of eye 18. Instrument 10 can be adapted to measure eye length (as also disclosed in PCT/AU2008/000434), or another instrument may be substituted for instrument 10 for that purpose.

It should be noted that the angles at which interrogating beams 24 are incident on eye 18 are measured with respect to the central optical axis 16, all interrogating beams being assumed to intersect axis 16 at the nodal point (not identified in FIG. 1) of eye 18 located on nodal plane 30. Thus the greatest peripheral angle that can be interrogated by instrument 10 is indicated at $\alpha$, this angle is being precisely defined by the geometry of the instrument. It might be noted that the angle at which the respective interrogating beam strikes retina 26 is not $\alpha$ because of the refraction of the cornea and the natural lens and is difficult to measure. The terms 'peripheral' and 'central' are therefore defined by reference to the angles at which rays are incident on the eye. Conventional vision correction modalities are only concerned with paraxial rays; that is, rays that are parallel with axis 16 and sufficiently close to the axis that they can pass through a normal pupil diameter. This effective central zone approximates to a circular area of the cornea defined by a cone of incident angles of about 10°. In this invention, the peripheral area of interest is an annular area of between about 20° and about 50° or a little more.

Figure 2:
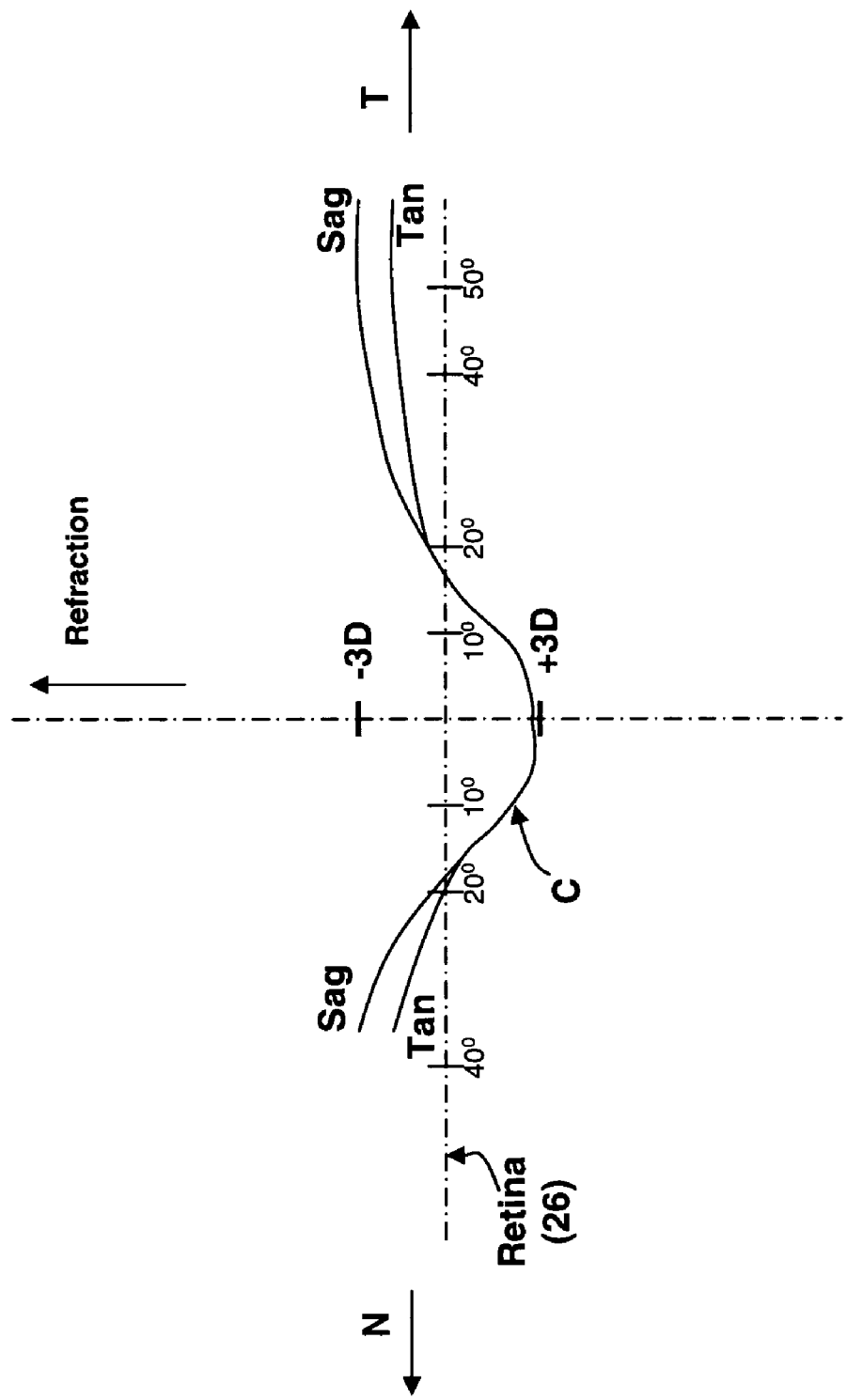
FIG. 2 is a line graph of refraction vs. peripheral field angle for the horizontal nasal—temporal meridian of a human eye as measured by the instrument of FIG. 1.

In operation, it will be normal to examine eye 18, with or without any prescribed corrective lens 19 using instrument 10. Thus, interrogating beams 24 are directed into eye 18, return beams 23 are directed back to unit 20 and detector means in unit 20 automatically determines aberrations along the beam path in eye 18 (and lens 19, if fitted) to allow the effective focal point in the eye to be determined relative to retina 26 at each spot where a beam 24 is incident. The graph of FIG. 2 is plot of the focal contour C in the horizontal meridian of the eye relative to retina 26 (the horizontal axis in FIG. 2) of the left eye of a young myope who has not previously been fitted with corrective lenses. The vertical axis shows refractive error, with positive and negative power indicated above and below the horizontal axis (ie, retina 26) respectively, the −3 D and +3 D points being indicated. Negative values mean that the focus is located behind (posterior to) retina 26 and positive values indicate that the focus is located in front of (anterior to) retina 26. The temporal and nasal sides of peripheral field of the left eye are indicated at T and N. In this diagram, peripheral degrees of field angle along the horizontal meridian of retina 26 are also indicated, it being noted that clear paraxial or central vision subtends about 10°. The sagittal and tangential foci are indicated by curves Sag and Tan respectively. Generation and interpretation of focal contour diagrams such as this are readily computed and displayed by instrument 10 for the benefit of the user or practitioner.

A number of observations can be made by inspection of FIG. 2, bearing in mind that the patient has not previously worn corrective lenses and assuming that the curvature of field—or focal plane—for both eyes is essentially the same:

For central vision, the patient is has a central refractive error of +3 D for which a −3 D correction would normally be prescribed; such a patient commonly being referred to as a '−3 D myope'.

For peripheral vision beyond about 20°, the patient exhibits substantial peripheral astigmatism and peripheral hyperopia. These would go undetected under conventional examination and be made worse by the prescription of conventional lenses that apply the same −3 D refractive adjustment over the whole lens, center and periphery.

The substantial peripheral hyperopia and central myopia indicate the presence or likelihood of progressive myopia. However, it is important to note that the prescription of conventional lenses to correct the myopia will add to the hyperopia and exacerbate eye growth and the progression of myopia.

The measured focal plane does not extend as far on the nasal side as on the temporal side because of occlusion by the nose when using the simple form of instrument of FIG. 1. Fortunately, it has been found that peripheral hyperopia on the temporal side is the greater stimulant for progressive myopia in the young.

Where the patient has previously been fitted with corrective lenses, it will be normal for the practitioner to examine each eye with its artificial lens (19) in place. If those lenses were of the conventional type, it is likely that substantial peripheral hyperopia will be observed with the lenses fitted. And, when eye 18 is examined without lens 19 in place, it is commonly found that myopes of −2 D and greater have myopic defocus in the periphery. In other words, the unaided eye would provide the stimulus for inhibiting further eye growth but the fitting of a conventional single power lens to correct for central refractive error induces peripheral hyperopia that stimulates continued eye growth and progressive myopia.

These observations will provide sufficient guidance to allow the practitioner to prescribe corrective glasses, contact lenses or othokerotology for both central and peripheral vision, provided it is emphasised that the peripheral power is the net power where the lens design applies the central power over the entire visual field. Because of the danger of error by conventional lens makers in this respect, and because of the desirability of obtaining good central vision and an acceptable level of difference between central and peripheral refractive power, it is highly desirable that the newly prescribed lenses are fitted and tested using an instrument like that of FIG. 1, or less desirably using visual charts, to confirm that (i) optimal central vision has been obtained and (ii) peripheral hyperopia has been eliminated. If, for example, it is found that best central vision is obtained with −3.50 D correction rather than the initially prescribed −3.0 D, then it is important to make sure that the periphery is not made hyperopic. Ideally, the prescription should bring the peripheral focal plane onto or in front of retina 26, despite the −0.50 D central adjustment.

The same procedure should then be followed on each successive examination of the patient to optimise central vision and to ensure that peripheral hyperopia is not present with lenses fitted. If central myopia is found to increase between visits despite this, it will be desirable to increase myopic defocus in the periphery to further inhibit excessive eye growth. In that event, however, it is desirable to check that the lenses so prescribed are acceptable to the patient; that is, that the increased difference between the central and peripheral powers is tolerable.

Those skilled in the art will appreciate that the desired peripheral refraction can be defined in three different ways where astigmatism is present:
(i) The spherical equivalent (circle of least confusion) is focused on or in front of the retina.
(ii) Only the tangential component is focused on or in front of the retina, the spherical equivalent and sagittal component are focused behind the retina.
(iii) Both, the sagittal and tangential component, and thus the spherical equivalent are focused on or in front of the retina.

While the last criterion is considered to have the best therapeutic effect, it is the most difficult to achieve in terms of optical design and attempts to meet this criterion can cause disturbing visual effects. For this reason, it is desirable (as already indicated) to assess acceptability with trial lenses. As already noted, because the profile of peripheral refractive error can vary widely between patients, it is beneficial in terms of treatment efficacy and wearability to generate custom or semi-custom lenses.

Figure 3:
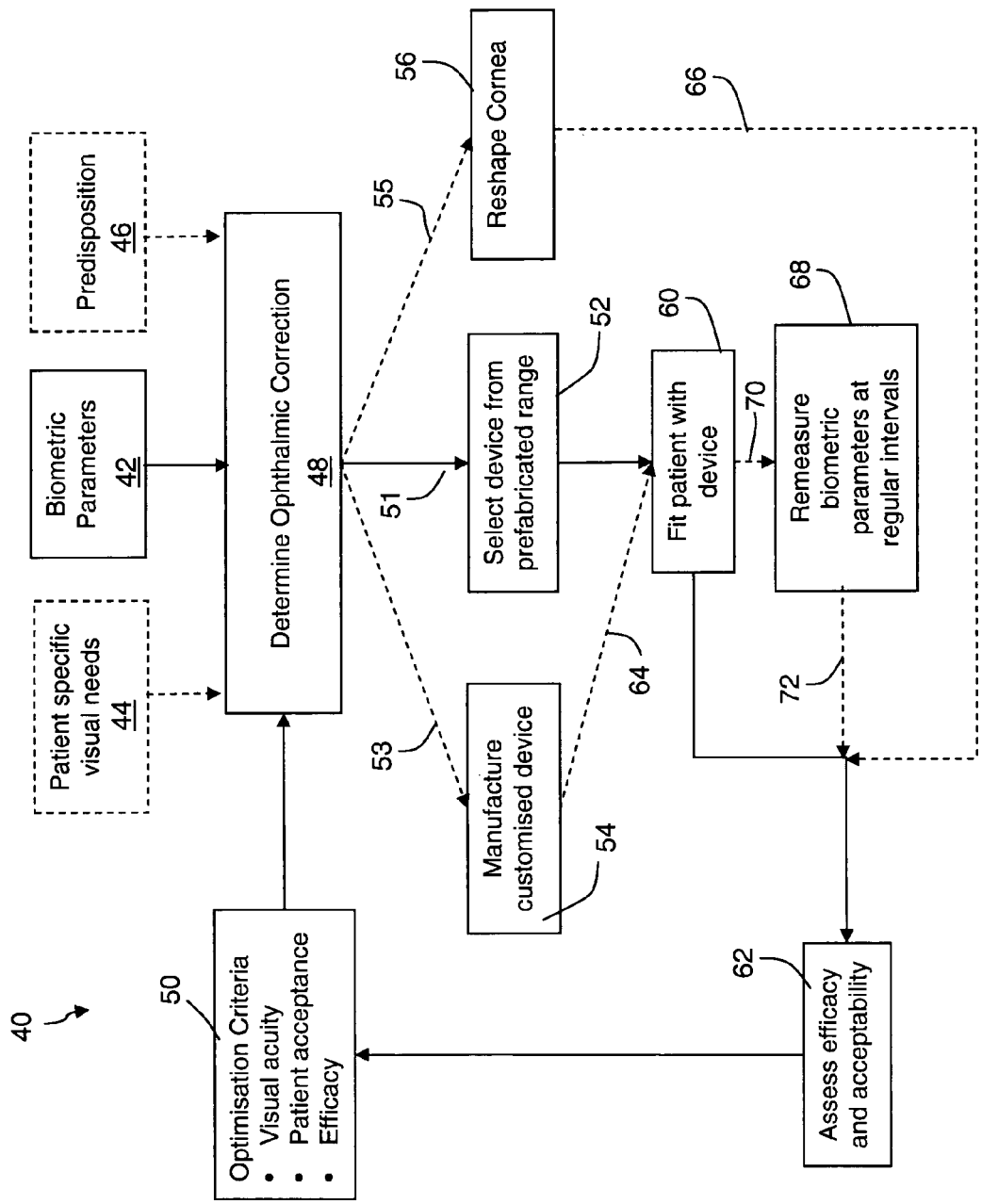
FIG. 3 is a flow chart depicting a first example of a process for prescribing and providing custom ophthalmic correction devices to a patient suffering from—or in danger of developing—progressive myopia.

The flow chart of FIG. 3 illustrates a group of methods 40 comprising the first example. In an input step 42, a number of biometric parameters can be determined, such as:
i) refractive error, preferably lower and higher order aberrations measured over a wide range of incident angles;
ii) eyeball length, (distance between cornea and retina) preferably both central and peripheral and preferably measured between the anterior surface, of the cornea and the anterior surface of the retina;
iii) pupil size and decentration;
iv) angle kappa (the angle between the pupil axis and the visual or optical axis which passes through the fovea);
v) strabismus (the tendency of an eye to turn in or out when viewing a central object); and
vi) cornea shape.

The first item (refractive error over a wide range of angles) is of prime importance and the second item is of secondary importance in the treatment and monitoring of progressive myopia where correction is by artificial lenses, the remaining items usually being of less value for optimizing vision when prescribing lenses. However, all items—especially the last—are likely to be important where the ophthalmic correction is by cornea re-shaping.

In addition to the input of biometric parameters 42, information 44 relating to the specific visual needs of the patient along with information 48 about the likely predisposition of the patient to progressive myopia, are desirably input. Examples of specific visual needs (44) are, on the one hand, 'close work' such as computer use, reading, sewing, drawing and the like where relatively poor peripheral vision can be tolerated but a wide field of good central visual acuity is desired, and on the other hand, driving, sports and outdoor activities where a narrow central field can be tolerated but good peripheral vision is desired. [The optional nature of inputs 44 and 46 is indicated by the use of dashed lines.]

All such information or data (42-46) is input to a computer-based design process 48 that determines or designs the ophthalmic correction required. Design process 48 comprises a computer program or algorithm adapted to generate a lens design and/or a desired cornea surface for (i) providing good central visual acuity for the eye and (ii) sufficient adjustment to the peripheral curvature of field to bring peripheral focus onto or in front of the retina and, preferably, sufficient to inhibit progressive myopia. Process 48 will normally a basic lens design process known in the art together with adjustments or presets for balancing the various items of input information, but provision for the practitioner to make some adjustment can be provided via the input of optimization criteria 50 to process 48 as feedback on the performance of trial lenses.

The resultant prescription or lens design can be output by design process 48 for various purposes:
at 51 to select a semi-custom prefabricated device (normally a spectacle or contact lens) from those held in stock by the practitioner or a manufacturer, as indicated at 52;
(ii) at 53 to enable the manufacture of a custom lens, as indicated at 54, or
(iii) at 55 to provide data needed to enable the cornea surface to be reshaped by laser or other means, as indicated at 56.

Arrows 53 and 55, respectively connecting process 48 with customised manufacture option (54) and cornea reshaping option (56), are shown in dashed lines as these options will probably be less common than the selection of a prefabricated lens indicated by solid-line arrow 51.

Once the prefabricated device has been selected and obtained at 52, it is fitted as a trial lens on the subject eye, as indicated at 60, for acceptability and efficacy evaluation, as indicated at 62. If it is not found to be sufficiently acceptable or efficacious, the optimisation criteria 50 are re-adjusted and the process is repeated. Acceptability will generally be determined by whether the patient considers that there is too much image distortion in the periphery or whether the field of (central) visual acuity is adequate. Efficacy will depend upon whether the combined refractive power of the lens and the eye has (i) optimised central vision and (ii) brought the desired peripheral focal plane far enough forward to be effective in inhibiting the progression of myopia. This assessment needs to be made by the practitioner examining the eye fitted with the prescribed lens (as described above) and by questioning the patient. It may need to be repeated at each successive consultation.

Essentially the same process of trial and optimisation (62 and 50) can be followed with a fully customised lens, as indicated by (i) dashed arrows 53 and 64, (ii) manufacturing step 54 and (iii) dashed arrow 64. Similarly, where cornea reshaping option 56 is selected, acceptability and efficacy can be assessed at 62—as indicated by dashed arrows 55 and 66—in substantially the same manner (except that there is no artificial lens) and the patient's cornea can be further shaped in situ if found to be unacceptable or deficient. It will be appreciated that the adjustments or optimisation effected in step 50 will differ between artificial lenses and cornea reshaping, the latter requiring a greater level of technical understanding than the former. However, those skilled in the art will appreciate this and will tailor the modes and levels of adjustment available in step 50 accordingly.

As already indicated, it is important for practitioners to follow-up patients suffering from progressive myopia to ensure that the treatment (adjustment of peripheral refraction) is working as hoped and, if not, to make further adjustments to bring the peripheral focus further forwards; that is, to increase the curvature of field in the periphery with minimal disturbance to central vision. This follow-up step is indicated at 68 and by dashed arrows 70 and 72 and applies to all corrective modalities 52, 54 and 56. The follow-up tests performed desirably include eye length, in addition to central and peripheral refraction for the eye alone and in combination with the prescribed lens or treatment. An increase in the central refractive power of the eye between visits, and/or and increase in eye length, will be indicative of the need to either increase the curvature of field in the periphery or to refer the patient for specialist care.

Figure 6:
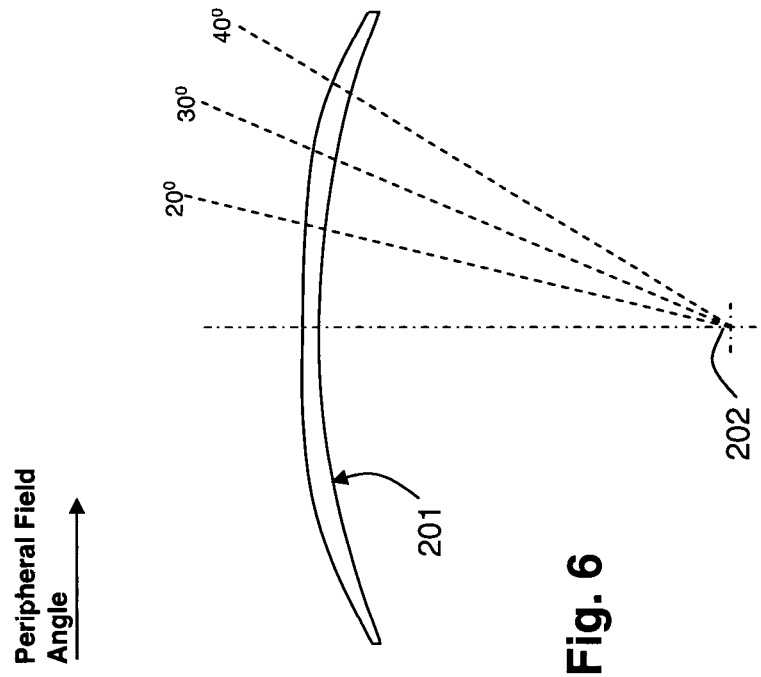
FIG. 6 is an indicative sectional plan view of a spectacle lens of the type indicated in FIG. 5 showing its notional contour, various peripheral angles being indicated in the horizontal temporal zone.
Figure 5:
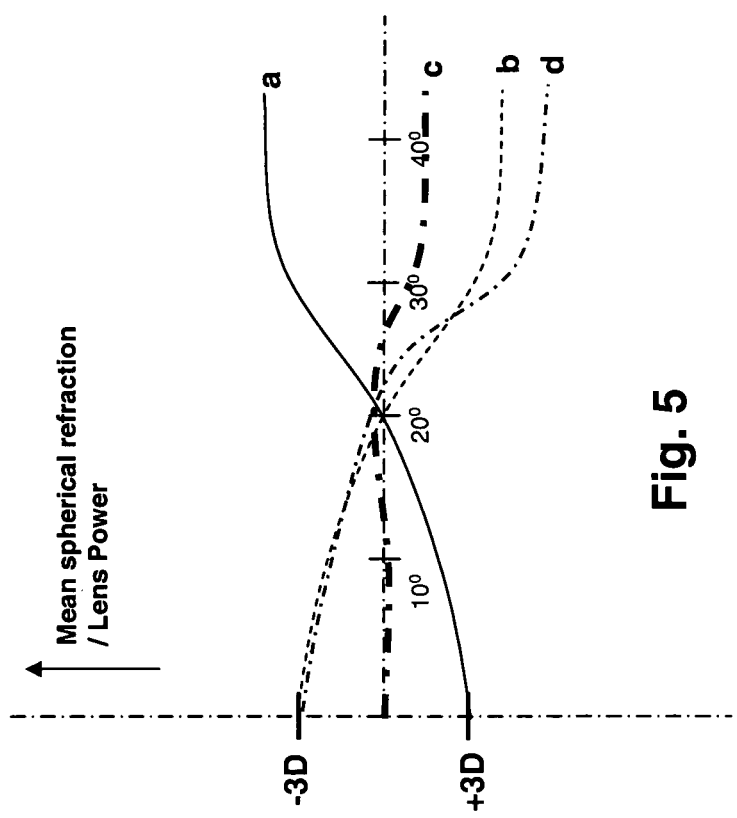
FIG. 5 is a series of line graphs of refraction vs. retinal eccentricity or peripheral angle over the horizontal temporal meridian for an exemplary eye and lens, showing adjustments made in accordance with the teachings of the present invention.

It will be appreciated by those skilled in the art that various computer programs are known and used for generating semi-custom and full-custom symmetric or asymmetric lens designs to optimise central vision. Similarly, computer programs are known and widely used for generating desired cornea contours from aberration data to achieve good central vision. Those skilled in computer programming in such a context will therefore be able to modify such programs to take peripheral aberrations into account; for example, the measured sagittal and tangential peripheral refraction profile for the nasal, temporal inferior and superior quadrants. For each peripheral angle, the corresponding power of the optical device is determined such that the desired peripheral focal plane(s) falls on or in front of the retina. [As noted above, the relevant focal plane can be the spherical equivalent of the tangential and sagittal foci, the sagittal focus alone or the tangential focus alone.] An example of a corrective lens for the eye of FIG. 2 is illustrated in FIGS. 5 and 6 and will be described below.

Figure 4:
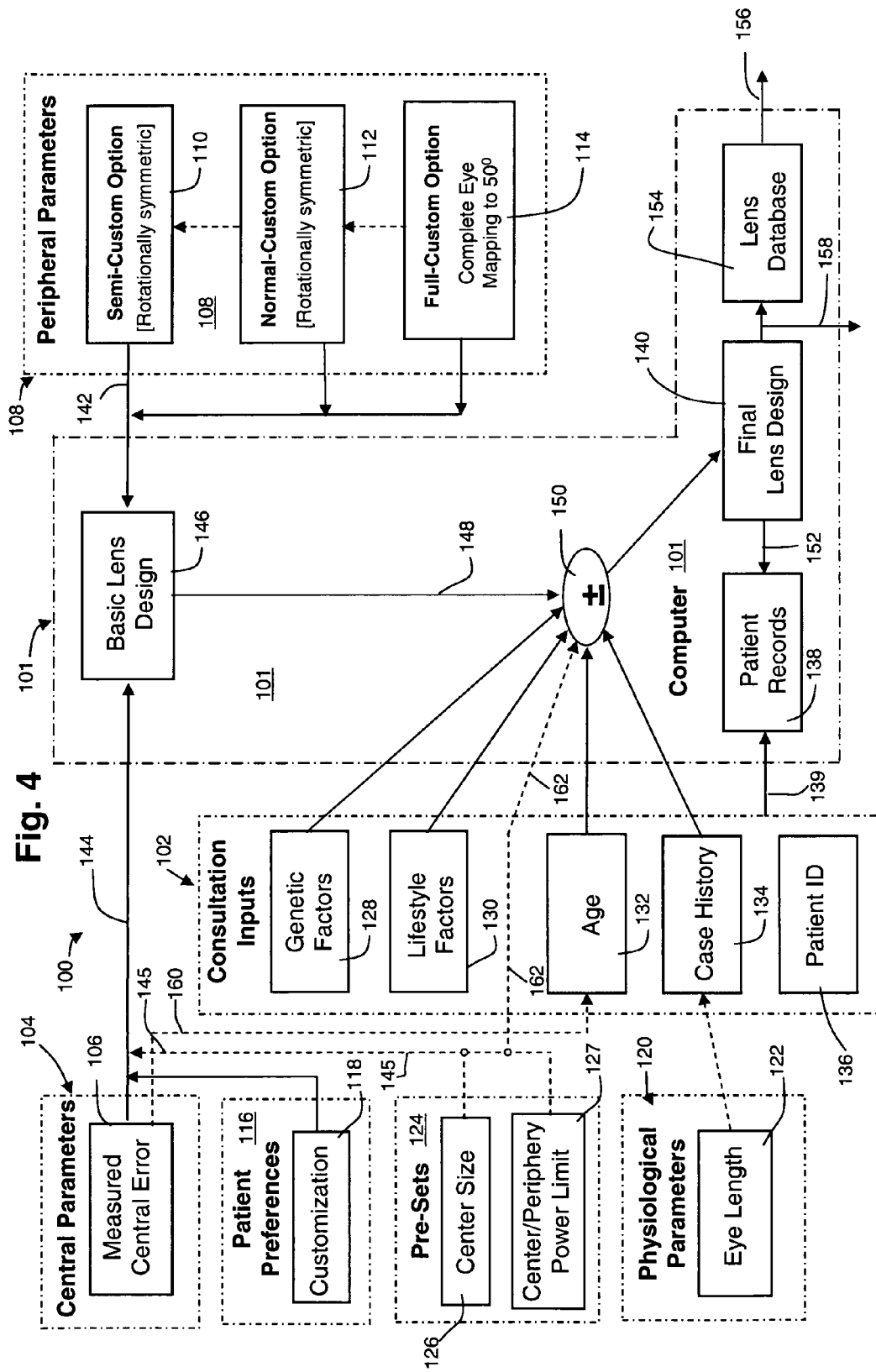
FIG. 4 is a flow chart illustrating a second example of a process like that indicated in FIG. 3.

In the system 100 of FIG. 4, which forms the second example or embodiment of the invention, a computer system 101 in a practitioner's clinic is adapted to receive and process a variety of inputs from the practitioner (not shown) during the examination and interview of a patient (not shown). These inputs include:

i) consultation inputs, generally indicated at 102, consisting of personal information gained by interview with the patient and his or her parents;

ii) measured central-vision parameters 104 for the patient's eyes, here represented by measured central refractive error 106, which may include only lower order aberrations or both lower order and higher order aberrations;

iii) measured peripheral vision parameters 108 for the patient's eyes that, in this embodiment, depend upon which of three customisation/cost options is selected by the patient and/or practitioner—namely, (i) a semi-custom option 110 that prescribes rotationally-symmetric pre-fabricated lenses from stocks held by a manufacturer, wholesaler or practitioner, (ii) a normal-custom option 112 that prescribes rotationally symmetric customised lenses tailored to correct the principal higher order aberrations of the patient's eyes given the need for rotational symmetry, and (iii), a full-custom option 114 that prescribes non-rotationally symmetric lenses tailored to correct higher order aberrations and allow for radial variation;

iv) patient preferences 116 about the type of lenses to be supplied, in this case represented by the degree of lens customisation 118, which in turn may influence the degree of customisation and cost, of the services and lenses, and;

v) additional physiological parameters 120 derived from additional assessments made by the practitioner or physicians; in this case, represented by a measurement of eye length, indicated at 122, made by the practitioner.

In addition, system 100 may offer the practitioner some discretionary pre-sets 124 that determine certain lens design parameters. In this case, a pre-set 126 is provided to allow the minimum size of the central 'clear zone' to be limited and a preset 127 is provided to limit the difference in refractive power between the central and peripheral zones of the lens. In general, however, it is preferable to limit practitioner access to such pre-sets as few practitioners will be sufficiently expert in lens design to understand the impacts of such limitations on the effectiveness of anti-myopia lenses.

Consultation inputs 102 are primarily those that can influence lens design and, thus, act as weighting factors. These are genetic factors 128, lifestyle factors 130, patient's age 132, and the patient's case history 134. In addition, consultation inputs 102 include patient identification information 136 necessary to establish a new patient record or account. The consultation inputs 102 are transferred to and recorded in the patient records 138 stored in computer 101 for each visit, as indicated by arrow 139.

For a new patient, therefore, system 100 basically operates as follows: The patient's ID 136 and relevant case history 134 are entered to establish a new patient record 138 and the patient's customisation preference 118 is obtained and entered to ensure that lenses with the appropriate degree of customization or cost are supplied from the final lens design or prescription 140 generated. The patient's preferences 116, in this case the selected customization option 118, will determine the peripheral parameters 108 that need to be measured by the practitioner and that are input to computer 101 as indicated by arrow 142. The practitioner also measures central refractive error and inputs the reading to computer 101 as indicated by arrow 144. The pre-sets 124 relating to center zone diameter 126 and the limitation of the difference between central and peripheral lens refractive power may be optionally input via line 145 (shown dashed) and line 144 to computer 101. All inputs on lines 142 and 144 are directed to a base lens design process or program 146 of a type known in the art.

In this example, it will be assumed that the default central clear zone is 20° measured radially from the center of the cornea of the eye and that it is unchanged by pre-set 126. Process 146 outputs the base lens design on line 148 for modification by an adjustment process algorithm 150 that generates the final lens design 140 having regard to weighting factors 128-134. Final lens design or prescription 140 is recorded in patient's records 138, as indicated by arrow 152.

The influence of the selected degree of customization will now be described in more detail.

The semi-custom option 110 for peripheral parameters 108 specified by patient customisation preference 118 designates a final lens design 140 that is rotationally symmetric in the periphery and is available from pre-manufactured stock. For this purpose, computer 101 includes a database 154 of commercial lenses such that the commercial lens which best matches the final lens design 140 can be identified by a manufacturer's code and output at 156 as a supply order; this output thus forming the semi-custom design. The peripheral measurements 110 required for this option (in this example) are two readings of refractive error at 30°, one in the nasal and the other temporal quadrant on the horizontal meridian. These are read by the practitioner and output at 142 to base lens design process 146, either as individual readings or as an average. Base lens design process 146 then performs the following functions: (i) averages (if required) the peripheral error readings, (ii) determines the relative peripheral refractive error (ie., central error minus averaged peripheral error) and (iii) determines the required power profile to shift the relative peripheral refractive error close to zero, while maintaining the pre-set central clear zone of 20° that provides good central vision. A form of normal-custom rotationally symmetrical lens design can be output at 158 but if desired.

While the normal-custom lens option 112 also provides a rotationally symmetric lens design that is also output on line 158, the design or prescription is better adapted to the patient's eye than the semi-custom lens of option 110. In this case, the practitioner takes at least four readings of peripheral refraction ranging from 20° to 50° in the nasal and temporal quadrants along the horizontal meridian and outputs each reading (error and angle) on line 142 to base lens design process 146, which averages (or integrates) paired nasal and temporal readings at each peripheral angle and, as before, computes (i) the relative peripheral refractive error and (ii) the required power profile to shift the relative peripheral refractive error to close to zero at the measured peripheral angles, while maintaining a pre-set clear zone of 20°. This new base lens design is output on line 148 for adjustment by process 150, as before. This time, however, it is the final output on line 158 that is selected (instead of that on line 156 representing the nearest commercial pre-manufactured lens) for transmission to a custom lens manufacturer, or for on-site custom production at the practitioner's facility.

The full-custom option 114 provides a non-rotationally symmetric lens design that best matches the patient's eye. Here, the practitioner makes a full map of the refractive errors (aberrations) of the eye in all quadrants and at all angles up to about 50° from the axis, including the central or on-axis refractive error. [The practitioner has the option of separately measuring the central (zero angle) refractive error and inputting that reading at 144, as before. However, it is preferred to input a complete 'eye map' at 142 when employing the full-custom option 114.

Base lens design process 146 then determines the relative peripheral refractive (aberrations) error around the eye and determines the power profile to shift it to close to zero at all radial and peripheral angles while maintaining a clear zone of acute central vision of about 20°. This base design is again fed on line 148 to adjustment process 150 and, after modification as determined by consultation inputs 102, to final lens design process 140 and custom design output 158 for transmission for manufacture.

The influence of the weighting factors of consultation inputs 102 will now be described for the second example.

In this embodiment, a proxy for genetic factors 128 is adopted; namely, the refractive errors of the four eyes of the patient's parents. These are added and the total is divided by 10 and the result is added to the determined peripheral power of base lens design 146 at 30° peripheral angle in adjustment process 150. Thus, if the refractive errors of the parent's eyes are 1.5 D, 2.0 D, 3.0 D and 2.5 D, which total 7 D, 0.7 D of myopic defocus needs to be added to the (near zero) base lens refractive error at 30° peripheral angle. As knowledge and experience grows this simple formula can be modified by the inclusion of other or additional indicators of genetic factors, such as the presence of specific genes in the patient.

Similarly, a simple proxy for lifestyle factors 130 can be provisionally adopted with sound justification; namely, the proportion of time the patient spends on average a day in outdoor activities. The justification arises from the well known fact that 'close work' such as reading and handheld video games and other indoor activities such as watching television contribute to myopia progression. In this example, the number of hours that the patient spends in outdoor activities on average per day is input into process 130 by the practitioner and output as an adjustment of minus 0.2 D for each hour to adjustment process 150. Thus, if the patient spends 1.5 hours per day on average in outdoor sports, any myopic defocus in the base lens design is reduced by 0.3 D.

It is also well known that the younger a patient is when he or she exhibits significant myopia, the more likely it is that the condition will progress. Accordingly, one of the weighting factors (132) relates to the age of the patient which is input by the practitioner. More specifically, for each year a myopic patient is younger than the expected age of puberty for that patient, (i) 0.25 D of myopic defocus is added to the corrective power at 30° peripheral angle and the central clear zone is reduced by 1° of radial angle to enhance the stimulus that inhibits continued eye growth. If desired, this bias can be increased where the patient's central refractive error is greater than 2.0 D, optional input line 160 to the age-related weighting factor 132 being indicated (in dashed form) for this purpose. It is to be noted, however, that the common observation that younger myopes are more likely to suffer from progressive myopia has been complicated hitherto by the use of conventional lenses which enforce peripheral hyperopia and, therefore, accelerate eye growth. Accordingly, it is desirable for young patients with significant myopia to be seen is more frequently by the practitioner and for eye length and on-eye lens performance to be checked at each visit and recorded in the patient's case history (134).

In addition, the 'case history' weighting factor 134 is intended to add a bias to adjustment process 150 by reflecting the increase or decrease in central myopic error over the preceding year. In this case, for each dioptre change in central refraction in the preceding year indicated by factor 134, (i) 0.50 D of myopic defocus is added to the corrective peripheral power at 30° peripheral angle and the central clear zone is reduced by 2°; that is, the myopic defocus at 30° is increased and the extent of the peripheral zone is increased in order to increase the inhibition of the growth in eye elongation provided by myopic peripheral defocus.

Optionally, as already indicated, the practitioner can additionally monitor eye elongation by direct measurement and use increased growth over the last year or two as an indicator of myopia progression and as a basis for computing the amount of added peripheral myopic bias required, in addition to (or less preferably) instead of an increase in central refractive error. Monitoring of eye length is also desirable for flagging pathologies where increasing central refractive error over time does not correlate with eye increasing eye length. In such cases, it may be desirable to refer the patient for specialist care.

It is of course recognised that the acceptability of a lens to a patient is of particular importance where the lens has been prescribed for a therapeutic purpose. While the lenses prescribed or generated by the methods of the present invention provide good central visual acuity, they can add significant myopic defocus in the periphery and even reduce the diameter of the central clear zone. This may lead to the patient complaining about a 'swimming sensation' when the head is moved or the body is in motion and, in the younger patient, may result in a lack of compliance. Accordingly some adjustments can be made to improve acceptability. First, adjustment process 150 can limit to the difference between the prescribed central and peripheral refractive powers; for example, 3.0 D has been found to be a suitable limit. Second, the practitioner can change the center/periphery power-limit pre-set 127 and, is optionally, both pre-sets 124 can be fed via line 162 (shown dashed) as over-rides on the adjustment process 150 that generates the final lens design 140. While care needs to be taken in exercising these pre-set over-rides because they may reduce inhibition of excessive eye growth, adjustments over successive visits should be able to both inhibit eye growth and improve acceptability.

FIG. 5 is a collection of graphs illustrating the effects of the adjustment process for an eye similar to that of FIG. 2. Note, however, that positive and negative refractive powers have been reversed in FIG. 5.

Graph a is the refractive error of natural eye 18 in the horizontal temporal meridian from 0° (ie, on the optic axis) to about 40°. It will be seen that the eye is 3.00 D myopic at the center, about 3.00 D hyperopic at about 40° and is without refractive error at about 20° on this meridian. A conventional corrective lens would have a power of −3.00 D at both the center and periphery and would therefore provide good central vision but would have 6.00 D of hyperopia in the periphery, resulting in a powerful stimulus for continued eye growth.

Graph b shows (in idealised form) the basic lens design (48, FIG. 3 or 146, FIG. 4) that would result from a reading of the central and peripheral refractive errors of eye 18, as represented by graph a; graph b being the inverse of graph a. Whether an unadjusted, semi-custom, normal-custom or full-custom basic design results depends on the number of refractive error measurements taken, the way they are averaged and whether or not the design is symmetrical. In substance, however, a lens with a refractive power profile of graph b would provide the best visual acuity for the patient as it places the image on the retina (horizontal axis) over a very wide angle of view from the center to the periphery.

Graph c indicates the desired or modified refraction profile from the adjustment process (150, FIG. 4) resulting from the input of the patient's history and preferences and from input of the practitioner's judgement a pre-set adjustments and the like. The desired profile provides good central vision out to about 20° and about 1.50 D of myopic defocus between about 30° and 45° in the periphery to inhibit or reduce further eye growth.

Graph d shows the lens design (power profile in the horizontal temporal meridian) needed to generate the diffraction profile of graph c in eye 18 when fitted with the prescribed lens (19). As noted, above, it is desirable to try the lens on the patient to check comfort and acceptability and efficacy in terms of the actual refraction profile of the eye and lens combination.

FIG. 6 is a diagrammatic horizontal sectional plan view of a spectacle lens 201 having a profile like that of graph d of FIG. 5, the peripheral angles from the nodal point of the eye 202 being indicated.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of determining a customised refractive correction for an eye of a patient to inhibit the progression of myopia in that eye, the eye having a central optic axis, a temporal quadrant, a nasal quadrant and a horizontal meridian passing through the temporal and nasal quadrants, said method comprising:
    measuring central aberrations within a central area of the eye that subtends an angle of less than 10° from the optic axis sufficient to specify a base central correction of said central aberrations that will provide clear vision in a central zone of the eye,
    measuring peripheral aberrations in an annular peripheral area of the eye that subtends angles greater than 20° from the optical axis sufficient to specify a base peripheral correction of said peripheral aberrations in a peripheral zone of the eye,
    modifying said base peripheral correction to incorporate an amount of myopic defocus determined by at least one of (a) the patient's predisposition to myopia, (b) the patient's lifestyle, and (c) the nature and degree of said peripheral aberrations of the eye, to thereby create a base customised refractive correction for that eye,
    determining said patient's predisposition to myopia by having regard to at least one of (a) the patient's genetic predisposition and (b) the patient's youthfulness, and
    having regard to said genetic predisposition by averaging the central refractive errors of the four eyes of the patient's parents to obtain an average myopic error, and increasing said myopic defocus according to the magnitude of said average myopic error.

2. A method according to claim 1 further comprising:
    having regard to said patient's youthfulness by determining how much younger the patient is than the patient's expected age of puberty, and
    at least one increasing said myopic defocus and the extent of said peripheral zone according said youthfulness.

3. A method according to claim 1, further comprising:
    determining said patient's lifestyle by having regard to the ratio of time spent by the patient indoors and outdoors, and
    at least one modifying the magnitude of said myopic defocus and the extent of said peripheral zone according the magnitude of said ratio.

4. A method according to claim 1, further comprising:
determining said patient's lifestyle by having regard to the importance assigned by the patient to the playing of outdoor sport, and
at least one reducing said myopic defocus and the extent of said peripheral zone in accordance with said assigned importance.

5. A method according to claim 1, further comprising:
determining said nature and degree of said peripheral aberrations by having regard to the degree of hyperopia or myopia in said peripheral area of the eye,
increasing said myopic defocus according to the magnitude of said hyperopia, and decreasing said myopic defocus according to the magnitude of said myopia.

6. A method according claim 1, further comprising:
applying said base customised refractive correction to the eye of the patient by shaping the cornea of the eye,
determining the performance of the eye with the shaped cornea by assessing at least one of (a) patient acceptance of peripheral blur, (b) acuity of central vision and (c) location of peripheral focus, and
modifying said customised base refractive correction to improve said determined performance in a further level of customisation.

7. A method according to claim 6, wherein:
said customised base refractive correction is modified by at least one of changing the degree of peripheral myopic defocus, varying the size of said peripheral area, and by enlarging the size of the central area.

8. A method according to claim 1, further comprising:
applying said base customised refractive correction to the eye of the patient by the fitting of an ophthalmic lens,
determining the combined performance of the eye and said lens by assessing at least one of (a) patient acceptance of peripheral blur, (b) acuity of central vision and (c) location of peripheral focus, and
modifying said customised base refractive correction to improve said determined performance in a further level of customisation.

9. A method of determining a customised refractive correction for an eye of a patient to inhibit the progression of myopia in that eye, the eye having a central optic axis, a temporal quadrant, a nasal quadrant and a horizontal meridian passing through the temporal and nasal quadrants, said method comprising:
measuring central aberrations within a central area of the eye that subtends an angle of less than 10° from the optic axis sufficient to specify a base central correction of said central aberrations that will provide clear vision in a central zone of the eye;
measuring peripheral aberrations in an annular peripheral area of the eye that subtends angles greater than 20° from the optical axis sufficient to specify a base peripheral correction of said peripheral aberrations in a peripheral zone of the eye, wherein measuring peripheral aberrations comprises making multiple measurements of peripheral aberration on or near the horizontal meridian of the of the eye and averaging said measurements to specify a base peripheral correction that is rotationally symmetric with respect to the optical axis of the eye; and
modifying said base peripheral correction to incorporate an amount of myopic defocus determined by at least one of (a) the patient's predisposition to myopia, (b) the patient's lifestyle, and (c) the nature and degree of said peripheral aberrations of the eye, to thereby create a base customised refractive correction for that eye.

10. A method of determining a customised refractive correction for an eye of a patient to inhibit the progression of myopia in that eye, the eye having a central optic axis, a temporal quadrant, a nasal quadrant and a horizontal meridian passing through the temporal and nasal quadrants, said method comprising:
measuring central aberrations within a central area of the eye that subtends an angle of less than 10° from the optic axis sufficient to specify a base central correction of said central aberrations that will provide clear vision in a central zone of the eye;
measuring peripheral aberrations in an annular peripheral area of the eye that subtends angles greater than 20° from the optical axis sufficient to specify a base peripheral correction of said peripheral aberrations in a peripheral zone of the eye, wherein measuring peripheral aberrations comprises making multiple measurements of peripheral aberration in multiple quadrants of the eye at multiple peripheral angles between 20° and 50° with respect to the optical axis of the eye, and wherein, said base peripheral correction is rotationally asymmetric with respect to the optical axis of the eye; and
modifying said base peripheral correction to incorporate an amount of myopic defocus determined by at least one of (a) the patient's predisposition to myopia, (b) the patient's lifestyle, and (c) the nature and degree of said peripheral aberrations of the eye, to thereby create a base customised refractive correction for that eye.

11. A method for providing a customised anti-myopia lens for inhibiting the progression of myopia in the eye of a patient, the eye having an optical axis, a temporal quadrant, a nasal quadrant and a horizontal meridian passing through the temporal and nasal quadrants, the method comprising:
generating a base lens design, having:
a central zone with a refractive power or powers for correcting central aberrations of the eye based upon central measurements of aberration of the eye made at angles of less than 10° with respect to the optical axis, and having
an annular peripheral zone surrounding said central zone with a refractive peripheral power or powers for correcting peripheral aberrations of the eye based upon peripheral measurements of aberration of the eye made at angles of at least 20° with respect to the optical axis, and
employing said base lens design to obtain a base lens,
fitting said base lens to the eye of the patient,
obtaining combined central aberration measurements of the combination of the base lens and the eye,
obtaining combined peripheral aberration measurements of the combination of the base lens and the eye,
modifying said peripheral power or powers of the base lens design using an algorithm having input parameters including at least one of (a) the patient's predisposition to myopia, (b) the patient's lifestyle, (c) acceptability of peripheral blur to the patient, (d) said combined central aberration measurements, and (e) said combined peripheral aberration measurements, to thereby create a customised lens design for the eye,
determining said patient's predisposition to myopia by having regard to at least one of (a) the patient's genetic predisposition, (b) the patient's youthfulness, and (c) the degree of hyperopic defocus in the periphery of the eye,
modifying the peripheral power or powers of the base lens design by at least one of increasing peripheral myopic defocus and by modifying the size of the peripheral zone of the base lens design, according to the determined predisposition, having regard to said genetic predisposition by averaging the central refractive errors of the patient's immediate blood relatives to obtain an average myopic error, and modifying the peripheral power or powers of the base lens design by at least one of increasing peripheral myopic defocus and the size of the peripheral zone according to the magnitude of said average myopic error, and employing said customised lens design to obtain a customised lens for the eye.

12. A method according to claim 11 further comprising:

having regard to said patient's youthfulness by determining how much younger the patient is than the patient's expected age of puberty, and modifying the peripheral power or powers of the base lens design by at least one of increasing peripheral myopic defocus and the extent of said peripheral zone according said youthfulness.

13. A method according to claim 11, further comprising:

determining said patient's lifestyle by having regard to the ratio of time spent by the patient indoors and outdoors, and modifying the peripheral power or powers of the base lens design by at least one of increasing peripheral myopic defocus, and by modifying the size of the peripheral zone of the base lens design, according to the determined ratio.

14. A method according to claim 11, further comprising:

determining said patient's lifestyle by having regard to the importance assigned by the patient to the playing of outdoor sport or vehicle driving, and modifying the peripheral power or powers of the base lens design by at least one of reducing peripheral myopic defocus and the size of said peripheral zone in accordance with said assigned importance.

15. A method according to claim 11, further comprising:

using said combined peripheral aberration measurements to modify the power of the power or powers of the peripheral zone of the base lens to ensure a degree of peripheral myopic defocus.

16. A method for providing a customised anti-myopia lens for inhibiting the progression of myopia in the eye of a patient, the eye having an optical axis, a temporal quadrant, a nasal quadrant and a horizontal meridian passing through the temporal and nasal quadrants, the method comprising:

generating a base lens design, having:

a central zone with a refractive power or powers for correcting central aberrations of the eye based upon central measurements of aberration of the eye made at angles of less than 10° with respect to the optical axis; and having an annular peripheral zone surrounding said central zone with a refractive peripheral power or powers for correcting peripheral aberrations of the eye based upon peripheral measurements of aberration of the eye made at angles of at least 20° with respect to the optical axis, and employing said base lens design to obtain a base lens, fitting said base lens to the eye of the patient, obtaining combined central aberration measurements of the combination of the base lens and the eye, obtaining combined peripheral aberration measurements of the combination of the base lens and the eye, modifying said peripheral power or powers of the base lens design using an algorithm having input parameters including at least one of (a) the patient's predisposition to myopia, (b) the patient's lifestyle, (c) acceptability of peripheral blur to the patient, (d) said combined central aberration measurements, and (e) said combined peripheral aberration measurements, to thereby create a customised lens design for the eye, using said combined central aberration measurements to change the central power of the base lens in both the central zone and the peripheral by the same amount so as to minimise the measured combined central aberration, and modifying said peripheral power or powers of the base lens to reverse said change of power in peripheral zone by the same amount, and employing said customised lens design to obtain a customised lens for the eye.

17. A method for providing a customised anti-myopia lens for inhibiting the progression of myopia in the eye of a patient, the eye having an optical axis, a temporal quadrant, a nasal quadrant and a horizontal meridian passing through the temporal and nasal quadrants, the method comprising:

generating a base lens design, having:

a central zone with a refractive power or powers for correcting central aberrations of the eye based upon central measurements of aberration of the eye made at angles of less than 10° with respect to the optical axis, and having an annular peripheral zone surrounding said central zone with a refractive peripheral power or powers for correcting peripheral aberrations of the eye based upon peripheral measurements of aberration of the eye made at angles of at least 20° with respect to the optical axis, wherein said peripheral measurements of aberration of the eye include multiple peripheral measurements of peripheral aberration on or near the horizontal meridian of the of the eye, and wherein the method includes the step of:

averaging said multiple peripheral measurements so as to generate a base lens design that is rotationally symmetric, employing said base lens design to obtain a base lens, fitting said base lens to the eye of the patient, obtaining combined central aberration measurements of the combination of the base lens and the eye, obtaining combined peripheral aberration measurements of the combination of the base lens and the eye, and modifying said peripheral power or powers of the base lens design using an algorithm having input parameters including at least one of (a) the patient's predisposition to myopia, (b) the patient's lifestyle, (c) acceptability of peripheral blur to the patient, (d) said combined central aberration measurements, and (e) said combined peripheral aberration measurements, to thereby create a customised lens design for the eye, and employing said customised lens design to obtain a customised lens for the eye.

18. A method for providing a customised anti-myopia lens for inhibiting the progression of myopia in the eye of a patient, the eye having an optical axis, a temporal quadrant, a nasal quadrant and a horizontal meridian passing through the temporal and nasal quadrants, the method comprising:

generating a base lens design, having:

a central zone with a refractive power or powers for correcting central aberrations of the eye based upon central measurements of aberration of the eye made at angles of less than 10° with respect to the optical axis, and having an annular peripheral zone surrounding said central zone with a refractive peripheral power or powers for correcting peripheral aberrations of the eye based upon peripheral measurements of aberration of the eye made at angles of at least 20° with resect to the optical axis, wherein said peripheral measurements of aberration of the eye include multiple peripheral measurements of peripheral aberration taken in multiple quadrants of the eye, said multiple quadrants including at least the temporal and nasal quadrants, at multiple peripheral angles between 20° and 50° with respect to the optical axis of the eye, so as to generate a base lens design that is rotationally asymmetric, and employing said base lens design to obtain a base lens, fitting said base lens to the eye of the patient, obtaining combined central aberration measurements of the combination of the base lens and the eye, obtaining combined peripheral aberration measurements of the combination of the base lens and the eye, modifying said peripheral power or powers of the base lens design using an algorithm having input parameters including at least one of (a) the patient's predisposition to myopia, (b) the patient's lifestyle, (c) acceptability of peripheral blur to the patient, (d) said combined central aberration measurements, and (e) said combined peripheral aberration measurements, to thereby create a customised lens design for the eye, and employing said customised lens design to obtain a customised lens for the eye.

19. A method for providing customised vision correction to an eye of a patient to inhibit the onset or progression of myopia in the eye, the eye having an optic axis, a cornea and a retina, an eye-length comprising the distance between the cornea and retina, a nasal quadrant and a temporal quadrant, the method comprising:

engaging the patient in a primary clinical consultation and determining primary patient data comprising:
a) date of birth or age,
b) severity of familial myopia,
c) a measurement of the central refractive error of the eye, and
d) at least one measurement of peripheral refractive error for the eye at angles relative to the optic axis of at least 20° in at least one of the temporal quadrant in terms of spherical equivalent, tangential component of astigmatism, and sagittal component of astigmatism, inputting said primary patient data into processor means having an algorithm adapted to generate a design or prescription for a primary customised lens having a central zone adapted to provide clear central vision for the eye and having a surrounding annular peripheral zone lying outside 20° relative to the optic axis and having a degree of myopic defocus determined by said algorithm, and fitting the patient with said primary customised lens, engaging the patient in a secondary clinical consultation subsequent to said primary clinical consultation and determining secondary patient data comprising:
a) a further measurement of the central refractive error of the eye without said primary customised lens in place,
b) a measurement of the combined central refractive error of the eye with said primary customised lens fitted to the eye,
c) a further measurement of peripheral refractive error of the eye without said primary customised lens in place,
d) a measurement of the combined peripheral refractive error of the eye and the lens with said primary customised lens in place,
e) a further measurement of eye-length, inputting said secondary patient data into said processor means and said algorithm to generate a secondary design or prescription for a secondary customised lens having a central zone adapted to provide clear central vision for the eye and having a surrounding annular peripheral zone lying outside 20° relative to the optic and having a degree of myopic defocus determined by said algorithm, and fitting the patient with said secondary customised lens.

20. A method for providing a customised anti-myopia lens for the eye of a patient, the eye having an optical axis, the method comprising:

generating a base lens design, having:
a central zone with a refractive central power for correcting central aberrations of the eye based upon central measurements of aberration of the eye made at angles of less than 10° with respect to the optic axis, and having
an annular peripheral zone surrounding said central zone with a refractive peripheral power or powers for correcting peripheral aberrations of the eye based upon peripheral measurements of aberration of the eye made at angles of at least 20° with respect to the optical axis, and employing said base lens design to obtain a base lens, fitting said base lens to the eye of the patient, obtaining combined central aberration measurements of the combination of the base lens and the eye to determine an adjustment of said central power to optimise central vision, making said power adjustment to both the central and peripheral zone of the lens, and removing said power adjustment from the peripheral zone, to create a customised lens design and providing said customised lens for the eye.

* * * * *